United States Patent
Fitzgerald

(10) Patent No.: US 7,387,159 B2
(45) Date of Patent: Jun. 17, 2008

(54) BLENDING SYSTEM FOR SOLID/FLUIDS MIXTURES

(75) Inventor: John Barry Fitzgerald, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 11/593,804

(22) Filed: Nov. 7, 2006

(65) Prior Publication Data
US 2007/0144739 A1 Jun. 28, 2007

(30) Foreign Application Priority Data
Dec. 2, 2005 (GB) ................... 0524598.0

(51) Int. Cl.
*E21B 47/00* (2006.01)
*E21B 33/13* (2006.01)

(52) U.S. Cl. .............. 166/250.14; 166/177.4; 166/253.1

(58) Field of Classification Search ............. None
See application file for complete search history.

(56) References Cited

U.S. PATENT DOCUMENTS

| | | | |
|---|---|---|---|
| 3,591,147 A * | 7/1971 | Anderson et al. ............ 366/142 |
| 4,450,576 A | 5/1984 | Lubecki et al. | |
| 5,319,314 A | 6/1994 | Chen | |
| 5,441,340 A | 8/1995 | Cedillo et al. | |
| 6,491,421 B2 | 12/2002 | Rondeau et al. | |
| 6,719,048 B1 * | 4/2004 | Ramos et al. .......... 166/250.15 |
| 2004/0007059 A1 | 1/2004 | Tudor | |

FOREIGN PATENT DOCUMENTS

| | | |
|---|---|---|
| GB | 1 413 098 | 11/1975 |
| WO | 2004/072621 A1 | 8/2004 |

OTHER PUBLICATIONS http://www.jme.co.uk/index.php?page=High Energy X-ray &cat=High Energy X-ray High Energy X-ray Betatron.
http://www.balteau.com/products.php?type=53 Baltospot portable X-ray generator.
'Multiphase well surveillance with a permanent downhole flowmeter' Webster et al Society of Petroleum Engineers, 2004, 90024, 1-8.

* cited by examiner

*Primary Examiner*—Zakiya W Bates
(74) *Attorney, Agent, or Firm*—Steven Gahlings; James McAleenan; Jody Lynn DeStefanis

(57) ABSTRACT

The disclosure concerns a method and a system for monitoring the composition of a cement slurry or wellbore service fluid, the method and system including one or more feeder units for solid particulate material; one or more mixing or blending units adapted to receive material from the feeder units; one or more outlet tubes to direct the cement slurry or wellbore service fluid to a storage facility or into a wellbore; and a control unit connected to at least one densitometer to monitor the density of the cement slurry or wellbore service fluid; wherein the densitometer comprises a generator free of radioactive material and capable of generating high-energy photons based on accelerating or decelerating electrons.

10 Claims, 3 Drawing Sheets

BLENDING SYSTEM FOR SOLID/FLUIDS MIXTURES

The present invention generally relates to an apparatus and a method for monitoring the mixing or blending process of fluids or slurries with solid compounds, particularly wellbore fluids such as fracturing fluids, cement slurries, and other well intervention.

CROSS-REFERENCE TO RELATED APPLICATIONS

This application claims the benefits of priority from Application Number 0524598.0, entitled "BLENDING SYSTEM FOR SOLID/FLUIDS MIXTURES," filed in the United Kingdom on 2 Dec. 2005, which is commonly assigned to assignee of the present invention and hereby incorporated by reference in its entirety.

BACKGROUND OF THE INVENTION

The pumping services sector within the oil and gas industry injects fluid into wells to stimulate production or to encase well bore tubulars. The fluids that are pumped usually include various chemicals and solid particulates. The chemicals are added to enhance the properties of the fluids or to make them more compatible with the hydrocarbon bearing formation. The particulates that are added to the fluids are used as propping agents, diverting agents, or as extenders that reduce volumetric cost, change volumetric density, or even enhance properties of the base fluid.

Sands (silicon, ceramic, resin), glass beads, and salts are examples of particulates that are added to fracture fluids, acids, and cements. All of these products come in defined densities and size ranges. The operations that employ these materials are pre-engineered for varying concentrations during the treatment dependent on the desired final results.

Within the industry, it is desirable to monitor the quality of the fluid within the system. This includes monitoring the concentration of particulates within the fluid. Current methods for quality control of the addition of particulates include: batch weighing, both pre- and post-job, mechanical metering during the addition of the particulates, or radioactive density measurements of the fluid slurries during operations.

Batch weighing provides quality control of the cumulative total product used, but does not provide quality control during on the fly operations for pre-engineered programs that vary the rate at which particulates are added during different phases of the injection.

Mechanical metering involves measuring the rate at which the particulate is added and the rate of the fluid prior to addition (clean rate) and then using these rates to calculate the particulate concentration in the slurry. The calculation for concentration is based on the knowledge of the density of the fluid and the particulate material. However, mechanical metering is prone to slippage and inaccuracies due to the efficiencies of the mechanical system being employed. The quality of the measurement is therefore limited.

Another method of measuring concentration is the use of radioactive densitometers, as described for example in the U.S. Pat. No. 5,441,340. The densitometer measures the absolute density of the slurry flowing in the pipe. In these measurements, a flux of photons is typically delivered through a pipe or other containment vessel; the flux of photons transmitted through the vessel and the contained fluid (or other material) is measured at an appropriately located detector, and this can be interpreted to yield fluid density. Given the density of each phase, it is then possible to determine the fractions given the mixture density.

Radioactive density measurements are the most accurate method of concentration measurements. The densities of the fluids and particulates are known prior to pumping and the radioactive density meter reads the absolute density of the slurry from which the particulate concentration can be calculated.

The currently deployed proppant concentration meter uses a radioisotope ("chemical") source to deliver gamma-rays of appropriate energy in order to provide a density measurement; given the density of the frac fluid and the additive (proppant), it is then simple to determine the proppant volume fraction. However, the deployment of a radioisotope source presents concerns over QHSE (possible exposure to radiation) and particularly security issues (loss or theft of radioactive "chemical" source), as well as licensing and transportation issues.

Various methods and apparatus have been suggested to remove the need for a radioactive source in the densitometer:

One alternative solution taught in the published U.S. Patent application 2004/0007059 is the use of an acoustic sensor.

Another alternative solution is described in the U.S. Pat. No. 6,491,421 and published International Patent application WO 2004/072621, both describing the use of a Coriolis flow meter to determine the density of a fracturing fluid.

In the light of the known state of the art, it is therefore an object of the present invention to provide an apparatus and method to monitor the mixing process of proppants and other solid particles into a fluid or slurry, particularly for use with wellbore service fluids and cementing slurries.

SUMMARY OF THE INVENTION

In accordance with an aspect of the invention, there are provided methods and systems for monitoring the composition of a cement slurry or wellbore service fluid, which methods and systems include at least one feeder unit for solid particulate material; one or more mixing or blending units adapted to receive material from the feeder units; one or more outlet tubes to direct the cement slurry or wellbore service fluid to a storage facility or into a wellbore; and a control unit connected to at least one densitometer to monitor the density of the cement slurry or wellbore service fluid; wherein the densitometer includes a high-energy photon generator capable of generating photons within an energy range of 10 KeV to 100 MeV, more preferably in the energy range of 10 KeV to 10 MeV, and even more preferably in the range of 100 KeV to 10 MeV The energy of the photon is preferably selected such that a sufficient number penetrates at least the equivalent of 5 mm of steel or 30 mm of fracturing fluid loaded with proppants. With regards to the high energy range, the photon energy is best selected such that sensitivity or absorption rate remains above a threshold that is conveniently detectable.

The generator comprises an electron accelerator (or decelerator). Possible generators for use in the present invention can be selected from a group comprising x-ray tubes, circular accelerators such as betatrons or synchrotrons, mini-microtrons, or linear electron accelerators. Hence to generate the photon flux it is no longer required to use a radioactive material.

An embodiment of the invention includes steps and means to monitor a parameter representative of the output radiation of the generator, thus allowing the system to compensate the density measurement for fluctuation in the output of the photon generator.

These and other aspects of the invention will be apparent from the following detailed description of non-limitative examples and drawings.

DETAILED DESCRIPTION

Figure 1:
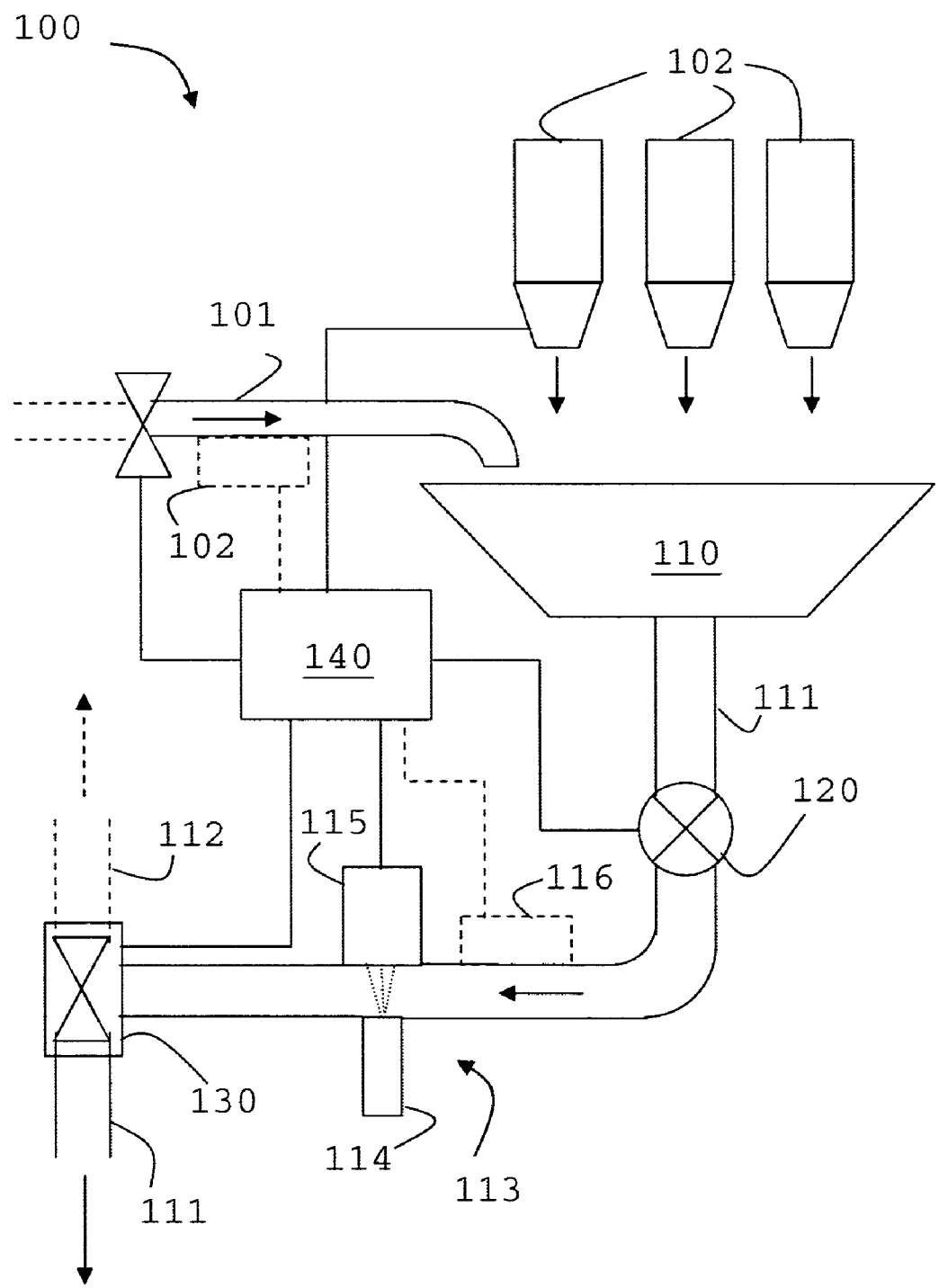
FIG. 1 illustrates basic elements of a known mixing or blending system.

The basic elements of a known fluid blending system are illustrated in FIG. 1. It illustrates a fluid blending system 100 for supplying for example a cement slurry or fracture fluid to a wellbore. The blending fluid system 100 is comprised of a one or more fluid supply tubes 101, and one or more storage containers 102 for chemicals and/or solid particulate materials. The supply tube 101 and the containers 102 are equipped to discharge into a mixer/blender 110, which could be for example a so-called vortex blender.

The blender has an outlet tube 111 connected to a pump 120 to discharge the fluid mixture or slurry to further equipment (not shown) such as high pressure pumps. An optional three-way valve 130 is shown to provide an optional recirculation path 112 which feeds either directly or indirectly back into the mixer 110. Coupled to the outlet tube 111 is a conventional nuclear densitometer 113 including a radiation source 114 with a small amount of radioactive material and a detector 115. The output of the detector is connected to a controller 140 that in turns is adapted to actuate feeding units 101, 102, the blender 110, the pump 120, and the outlet valve 130.

In addition, one or more flowmeters 102, 116 may be included to measure further flow parameters such as mass flow rate etc in the outlet tube 111 or any of the inlets 101.

In operation, a suitable base fluid such as brine is pumped through the supply line 101 and released as a controlled volume flow into the mixing tub 110. Suitable measured amounts of particulate components such as sand, fibers or other proppant material, cement and chemicals such as polymer granulate, guar and the like are added through the particulate feeders 102. The blending unit 110 mixes the different component and the resulting multiphase flow is discharged through the outlet tube 111 into a storage tank (not shown) or directly to the location where is slurry is to be applied. In the present example, this location is a wellbore (not shown).

As the full stream of the multiphase fluid flows through discharge tube 111, the nuclear densitometer 113 measures the density of the fluid. The nuclear densitometer 113 transmits the density measurement to the controller unit 140. The controller unit 140 is programmed with the respective densities of the components and can hence calculate the amount of the particulate material in the stream either directly or through a model. Further measurements performed using the flowmeters 102,116 can be used to derived and control further parameters of the mixing process.

As described above, there are many problems associated with using a nuclear source 114 in the densitometer 113. For instance, interstate and international transport of nuclear densitometers can be a difficult process, safe handling and transporting of the nuclear densitometers is a concern, and the people operating the nuclear densitometers have to be certified or licensed by the proper regulatory agency. Such factors make nuclear densitometers undesirable to use.

An alternative sourceless approach as proposed by the present invention to eliminate the radioisotope source by replacing it with a non-radioactive generator of suitable photon fluxes, using an electrical photon generator that generates high energy photons through the acceleration or deceleration of electrons. Such generators have a number of advantages: In particular, when not in operation, there is no radiation risk presented since the device can be remotely switched off.

Figure 2:
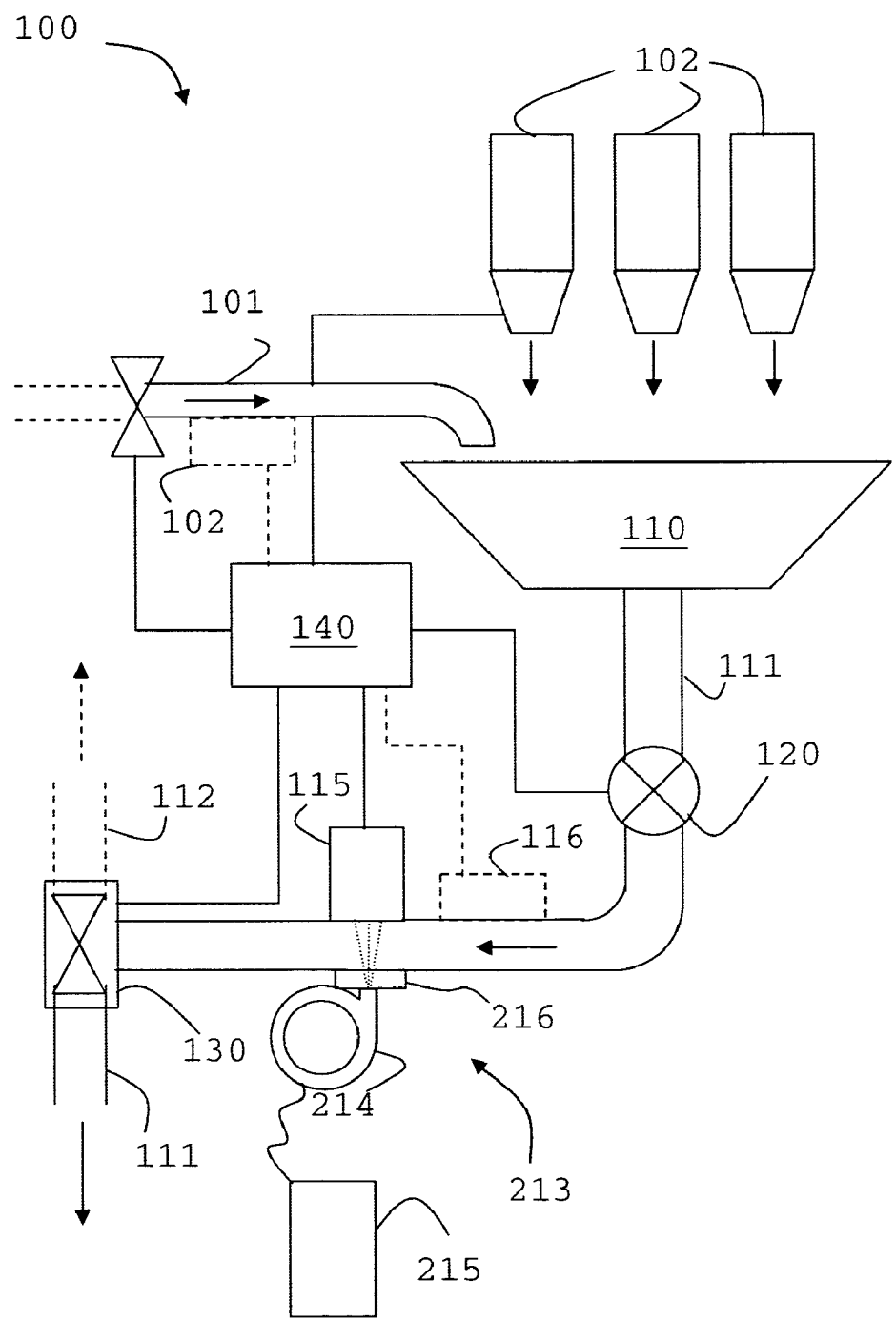
FIG. 2 shows further details of the system of FIG. 1 together with examples of the present invention.

In the case of the present application as shown in FIG. 2, a suitable photon source would be a Betatron accelerator-based photon generator 213. The Betatron is a well-known accelerator design which uses a varying magnetic field to accelerate electrons (or other particles) to high energies.

An advantage of the Betatron is that the magnetic field used to accelerate the particles and the field used to contain them in a circular orbit are linked, so that the orbit radius remains constant for all energies. The betatron includes a compact "doughnut"-shaped accelerator 214 supplied by an electrical power source 215, which can generate a photon flux of energy and intensity comparable (or superior) to a typical nuclear source. A small (~8" (25 cm)) device can generate radiation of comparable energy to a logging (or density) chemical source such as Cs-137 or Co-60. Such generators are commercially available for example from JME Ltd of Lowstoft, Suffolk, United Kingdom, in a 6 MeV and 7.5 MeV variant, and are typically used in material testing as a high energy X-ray source. Their dose rate is 3R and 5R, respectively , per minute at 1 m in air.

As an alternative to the betatron, a portable x-ray generator can be used such as provided for example under the tradename Baltospot by Balteau S. A. of 4681 Hermalle-sous-argenteau, BELGIUM with energies at 160, 235 and 300 KeV. For the use of these lower energy photon, the wall of the pipe 111 may be equipped with X-ray transparent windows.

In will be appreciated by a skilled person that the with respect to the other components of the densitometer, such as detector/counter and evaluation programs, the replacement of the radioactive source by a photon generator requires only insignificant adaptations.

A major advantage of the novel approach is that the measurement principle and interpretation would remain essentially identical to the current radioisotope-based measurement, however without the use of any radioactive material. The generator 214 would be deployed effectively as a simple, electrically-powered replacement for the radioactive "chemical" source in a similar geometry (see FIG. 1). Such measurements are well characterized as a means of determining density and are commonly used in a number of industries, notably for medical measurements and for mechanical engineering inspection measurements. However it should be noted that many known conventional X-ray generators do not provide fluxes of sufficiently high energies to penetrate thick pipe walls and several inches of relatively high density fluid.

Although the radiation source proposed by the present invention is preferably a Betatron or X-ray tube, other electron accelerator designs with appropriate output energy can be used. The "appropriate energy" means sufficient to penetrate the containment vessel or pipe walls, as well as the fluid mixture, and low enough to provide sufficient density sensitivity to yield particulate or proppant volume fraction to the required precision.

The proposed system has a number of advantages over the known radiation densitometer as listed below:

1. No nuclear sources are required;
2. The measurement is essentially the same as the current measurement, other than the substitution of an electrical radiation generator for the "chemical" radioisotope source;
3. Fairly simple and robust electrical and electronic technology is required to measure the fluid density;
4. Low cost;
5. No moving parts;
6. The measurement effectively provides a direct measurement of density;
7. Photon attenuation measurements are not dependent on environmental conditions such as temperature, nor on structural properties of the mixture;
8. The measurement can "see through" a pipe or other vessel;
9. Radiation fields, other than in the main beam, are generally low. As a result, shielding requirements are moderate.

However, electrical radiation generators do not have the intrinsically stable output of a radioisotope source. This means that it may be required to provide a monitor or reference measurement shown in FIG. 2 as second detector 216 on or near the generator 214 to measure the output radiation flux.

Essentially, the measurement then comprises the ratio of measured transmitted flux through the slurry or multiphase fluid to the reference flux at the radiation source.

Figure 3:
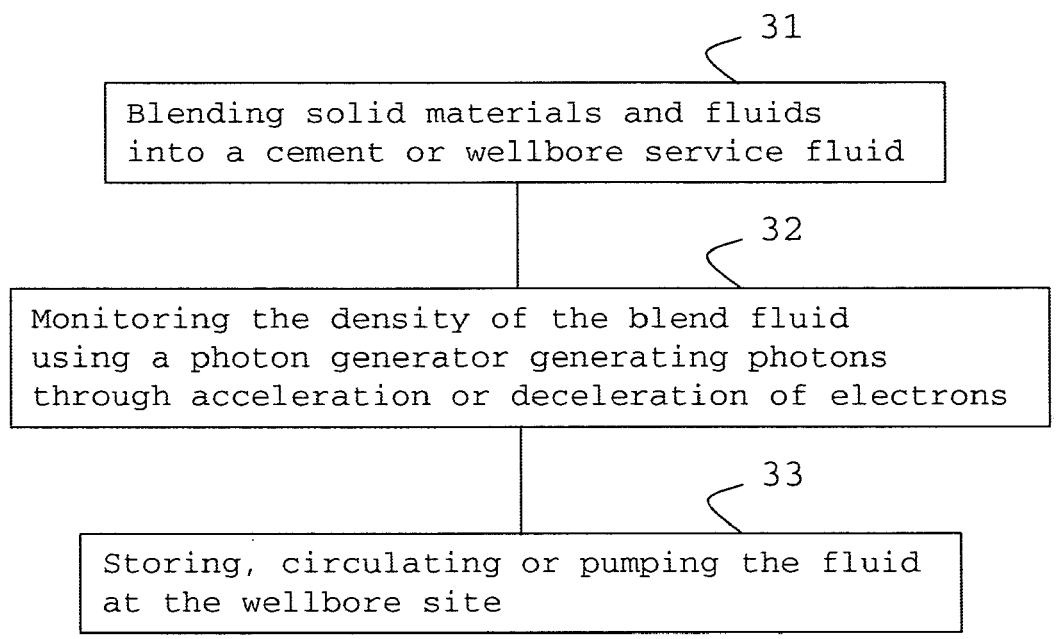
FIG. 3 shows steps of a method in accordance with an example of the invention.

In FIG. 3, steps in accordance with an example of the invention are shown, including a step 31 of blending solid materials and fluids into a cement or wellbore service fluid, a step 32 of monitoring the density of the blend fluid using a photon generator generating photons through acceleration or deceleration of electrons and a step 33 of Storing, circulating or pumping the fluid at the wellbore site.

The invention claimed is:

1. A system for monitoring the composition of a cement slurry or wellbore service fluid, said system comprising:
   one or more feeder units for solid particulate material; one or more mixing or blending units adapted to receive material from the feeder units;
   one or more outlet tubes to store, circulate or pump the cement slurry or wellbore service fluid at the site of a wellbore; and
   a control unit connected to at least one densitometer to monitor the density of the cement slurry or wellbore service fluid; wherein the densitometer comprises a betatron configured to generate photons.

2. The system of claim 1, wherein the betatron generates photons in the energy range of 10 KeV to 100 MeV.

3. The system of claim 1, wherein the betatron generates photons in the energy range of 10 KeV to 10 MeV.

4. The system of claim 1, further comprising a monitor to detect a parameter representative of output radiation generated by the betatron.

5. The system of claim 1, further comprising a comparator unit to correct the densitometer for variations in the output level of the betatron.

6. A method of monitoring the composition of a cement slurry or wellbore service fluid, said method comprising the steps of:
   supplying continuously, quasi-continuously or in batches to a blender or mixing unit at least one base fluid and at least one solid particulate material;
   mixing or blending the supplied material in the blender or mixing unit;
   monitoring the density of the cement slurry or wellbore service fluid using at least one densitometers,
   wherein the densitometer comprises a betatron for producing photons; and
   pumping, circulating or storing the cement slurry or wellbore service at the site of a wellbore.

7. The method of claim 6, wherein the betatron produces photons in the range of 10 KeV to 100 MeV.

8. The method of claim 6, wherein the betatron produces photons in the range of 10 KeV to 10 MeV.

9. The method of claim 6, further comprising the step of monitoring a parameter representative of an output of the betatron.

10. The method of claim 6, further comprising the step of correcting the densitometer for variations in the output level of the betatron.

* * * * *